(12) United States Patent
Treado et al.

(10) Patent No.: US 7,218,822 B2
(45) Date of Patent: May 15, 2007

(54) METHOD AND APPARATUS FOR FIBERSCOPE

(75) Inventors: Patrick J. Treado, Pittsburgh, PA (US); Matthew Nelson, Harrison City, PA (US); Joseph E. Demuth, Pittsburgh, PA (US)

(73) Assignee: Chemimage Corporation, Pittsburgh, PA (US)

( * ) Notice: Subject to any disclaimer, the term of this patent is extended or adjusted under 35 U.S.C. 154(b) by 128 days.

(21) Appl. No.: 10/956,044

(22) Filed: Oct. 4, 2004

(65) Prior Publication Data

US 2006/0051036 A1    Mar. 9, 2006

(51) Int. Cl.
G02B 6/06 (2006.01)
G01J 3/44 (2006.01)
A61B 1/06 (2006.01)

(52) U.S. Cl. .................. 385/117; 356/301; 600/177
(58) Field of Classification Search ................ 385/116, 385/117, 119; 356/301; 600/160, 177, 181
See application file for complete search history.

(56) References Cited

U.S. PATENT DOCUMENTS

| | | | |
|---|---|---|---|
| 5,194,912 A | 3/1993 | Batchelder et al. |
| 5,377,003 A | 12/1994 | Lewis et al. |
| 5,377,004 A | 12/1994 | Owen et al. |
| 5,394,499 A | 2/1995 | Ono et al. |
| 5,442,438 A | 8/1995 | Batchelder et al. |
| 5,493,443 A | 2/1996 | Simon et al. |
| 5,528,393 A | 6/1996 | Sharp et al. |
| 5,623,342 A | 4/1997 | Baldwin et al. |
| 5,689,333 A | 11/1997 | Batchelder et al. |
| 5,710,626 A | 1/1998 | O'Rourke et al. |
| 5,862,273 A | 1/1999 | Pelletier |
| 5,866,430 A | 2/1999 | Grow |
| 5,901,261 A | 5/1999 | Wach |
| 5,911,017 A | 6/1999 | Wach et al. |
| 5,943,122 A | 8/1999 | Holmes |
| 5,974,211 A | 10/1999 | Slater |

(Continued)

FOREIGN PATENT DOCUMENTS

WO    WO9511624    5/1995

OTHER PUBLICATIONS

Morris, Hoyt and Treado, "Imaging Spectrometers for fluorescence and Raman Microscopy; Optie and Liquid Crystal Tunable Filter," Applied Spectroscopy, vol. 48, No. 7, 1994.

(Continued)

*Primary Examiner*—Alessandro Amari
(74) *Attorney, Agent, or Firm*—Duane Morris, LLP

(57) ABSTRACT

The disclosure generally relates to a method and apparatus for a fiberscope. In one embodiment, the disclosure relates to a chemical imaging fiberscope for imaging and collecting optical spectra from a sample having at least one illumination fiber for transmitting light from a first an a second light source to a distal end of a fiberscope; a dichroic mirror disposed at said distal end of the fiberscope such that light from said first light source passes substantially straight through said mirror and light of a predetermined wavelength from said second light source is substantially reflected by said mirror toward said sample to thereby illuminate said sample; and at least one collection fiber for receiving light from said illuminated sample and transmitting the received light to an optical device.

51 Claims, 11 Drawing Sheets

U.S. PATENT DOCUMENTS

| | | |
|---|---|---|
| 6,002,476 A | 12/1999 | Treado |
| 6,006,001 A | 12/1999 | Alfano et al. |
| 6,088,100 A | 7/2000 | Brenan et al. |
| 6,091,872 A | 7/2000 | Katoot |
| 6,134,365 A * | 10/2000 | Colvin ........................ 385/116 |
| 6,222,970 B1 * | 4/2001 | Wach et al. ................. 385/115 |
| 6,456,769 B1 * | 9/2002 | Furusawa et al. ........... 385/117 |
| 6,483,641 B1 | 11/2002 | MacAulay |
| 6,485,413 B1 | 11/2002 | Boppart et al. |
| 6,571,117 B1 | 5/2003 | Marbach |
| 6,687,534 B2 * | 2/2004 | Tsujita ........................ 600/476 |
| 6,697,665 B1 | 2/2004 | Rava et al. |

OTHER PUBLICATIONS

Morris, Hoyt, Miller and Treado, "Liquid Crystal Tunable Filter Raman Chemical Imaging," Applied Spectroscopy, No. 50, No. 6, Jun. 1996.

Skinner, Cooney, Sharma and Angel, "Remote Raman Microimaging Using an AOTF and a Spatially Coherent Microfiber Optical Probe," Applied spectroscopy, vol. 50, No. 8, 1996.

* cited by examiner

METHOD AND APPARATUS FOR FIBERSCOPE

The instant application claims the filing-date benefit of application Ser. Nos. 10/934,885 and 10/935,423, filed Sep. 3, 2004 and Sep. 7, 2004, respectively. Each of said applications claims the filing date benefit of application Ser. No. 09/619,371 (now U.S. Pat. No. 6,788,860) filed Jul. 19, 2000, which itself claims the filing-date benefit of Provisional Application No. 60/144,518 filed Jul. 19, 1999. Reference is also made to application Ser. Nos. 09/976,391 (now U.S. Pat. No. 6,734,962) and Ser. No. 09/064,347 (now U.S. Pat. No. 6,002,476) which are assigned to the assignee of the instant application. The specifications of each of the above-identified applications is incorporated herein in its entirety for background information.

BACKGROUND

Chemical imaging combines optical spectroscopy and digital imaging for the molecular-specific analysis of materials. Raman, visible, near infrared (VIS/NIR) and Fluorescence chemical imaging have traditionally been performed in laboratory settings using research-grade light microscope technology as the image gathering platform. However, chemical imaging is applicable to in situ industrial process monitoring and in vivo clinical analysis. The application of chemical imaging outside the research laboratory has been limited by the lack of availability of stable imaging platforms that are compatible with the physical demands of industrial process monitoring and clinical environments. Both industrial and clinical settings often require compact, lightweight instrumentation suitable for the examination of remote areas that are inaccessible to conventional chemical imaging instrumentation and involve harsh chemicals in hostile areas. In addition, for in vivo cardio-vascular clinical applications, the presence of blood and bodily fluids limits the viewing, identification and ability to perform in vivo optical measurements of suspect areas.

Raman spectroscopy is one of the analytical technique that is broadly applicable and can be used for chemical imaging. Among its many desirable characteristics, Raman spectroscopy is compatible with samples in aqueous environments and can be performed on samples undergoing little or no sample preparation. The technique is particularly attractive for remote analysis via the use of optical fibers. By employing optical fibers for light delivery and collection the light source and light detector can be physically separated from the sample. This remote attribute is particularly valuable in sensing and analysis of samples found in industrial process environments and living subjects.

In a typical fiber-optic based Raman analysis configuration, one or more illumination fiber-optics deliver light from a light source (typically a laser) through a laser bandpass optical filter and onto a sample. The laser bandpass filter allows only the laser wavelength to pass while rejecting all other wavelengths. This purpose of the bandpass filter is to eliminate undesired wavelengths of light from reaching the sample. Upon interaction with the sample, much of the laser light is scattered at the same wavelength as the laser. However, a small portion of the scattered light (1 in 1 million scattered photons on average) is scattered at wavelengths different from the laser wavelength. This phenomenon is known as Raman scattering. The collective wavelengths generated from Raman scattering from a sample are unique to the chemistry of that sample. The unique wavelengths provide a fingerprint for the material and are graphically represented in the form of a spectrum. The Raman scattered light generated by the laser/sample interaction is then gathered using collection optics which directs the light through laser rejection filter which eliminates the laser light, allowing only Raman light to be transmitted. The transmitted light is then coupled to a detection system via one or more collection fiber-optics.

Previously described Raman fiber optic probe devices have several limitations. First, current fiber-optic-based Raman probes are sensitive to environmental variability. These devices often fail to function properly when the probe is subjected to hot, humid and/or corrosive environments. Several fundamental differences from current devices have been incorporated into the chemical imaging fiberscope design described here that address the environmental sensitivity issue. First, an outer jacket (or housing) that is mechanically rugged and resistant to varying temperatures and high humidity has been incorporated into the fiberscope design. Second, an optically transparent window that withstands harsh operating environment has been built into the probe at the fiberscope/sample interface. Normally, incorporation of a window into a probe would introduce a significant engineering problem. As emitted illumination light passes through the window and onto the sample, a portion of this light is back reflected by the window's inner and outer surfaces. In the prior art, this undesired back reflected light is inadvertently introduced into the collection fibers along with the desired Raman scattered light. The back reflected light corrupts the quality of the analysis. This problem is addressed in the current design by careful engineering of the aperture of the collection bundle taking into account the numerical apertures (NA) associated with the collection bundle fibers and collection lenses.

Previous probe designs are also inadequate because of the environmental sensitivity of the spectral filters that are employed in the devices. The chemical imaging fiberscope design of the current disclosure relies on spectral filter technologies that are remarkably immune to temperature and humidity. Past spectral filters have traditionally been fabricated using conventional thin film dielectric filter technology which are susceptible to temperature and humidity induced degradation in the filter spectral performance. The spectral filters described in the present disclosure employ highly uniform, metal oxide thin film coating material such as $SiO_2$ which exhibits a temperature dependent spectral band shift coefficient an order of magnitude less than conventional filter materials. The improved quality and temperature drift performance of metal oxide filters imparts dramatically improved environmental stability and improved Raman performance under extreme conditions of temperature and humidity.

Another limitation of current probe technologies is that none combine the three basic functions of the chemical imaging fiberscope: (1) video inspection; (2) spectral analysis; and (3) chemical image analysis in an integrated, compact device.

Raman chemical imaging integrates the molecular analysis capabilities of Raman spectroscopy with image acquisition through the use of electronically tunable imaging spectrometers. In Raman chemical imaging, scattered Raman light is shifted in wavelength from the wavelength of the illuminating light. For example, Raman illumination at 532 nm can excite molecular vibrations in the sample at for example, 4000 $cm^{-1}$ to produce scatter Raman light at lower and higher wavelengths of 439.3 nm and 647.5 nm, respectively. The Raman wavelength can be in the range of −4000–4000 $cm^{-1}$. This produced Raman features 4000 cm$^{-1}$ above the illuminating wavelength. Several imaging spectrometers have been employed for Raman chemical imaging, including acousto-optical tunable filters (AOTFs) and liquid crystal tunable filters (LCTFs). For Raman imaging, LCTFs are clearly the instrument of choice based on the following demonstrated figures of merit: spatial resolving power (250 nm); spectral resolving power (<0.1 cm$^{-1}$); large clear aperture (20 mm); and free spectral range (0–4000 cm$^{-1}$). LCTF's can also be designed by those skilled in the art to operate over different ranges of detection wavelengths that depend on the application from, for example, 400–720 nm, 650–1100 nm, 850–1800 nm or 1200–2400 nm. AOTFs and LCTFs are competitive technologies. AOTFs suffer from image artifacts and instability when subjected to temperature changes.

Under normal Raman imaging operation, LCTFs allow Raman images of samples to be recorded at discrete wavelengths (energies). A spectrum is generated corresponding to thousands of spatial locations at the sample surface by tuning the LCTF over a range of wavelengths and collecting images systemically. Contract is generated in the images based on the relative amounts of Raman scatter or other optical phenomena such as luminescence that is generated by the different species located throughout the sample. Since a spectrum is generated for each pixel location, chemometric analysis tools such as Cosine Correlation Analysis (CCA), Principle Component Analysis (PCA) and Multivariate Curve Resolution (MCR) are applied to the image data to extract pertinent information.

Chemical imaging can be performed not only in a scattering mode at high resolution as done for Raman chemical imaging using laser illumination, but it can also be conducted for broadband incident illumination (wavelength>10 cm$^{-1}$) at corresponding reduced spectral resolution (wavelength>10 cm$^{-1}$). This broadband illumination and reduced resolution spectroscopy can be done in the UV wavelength (200–400 nm), VIS wavelength (400–780 nm) and NIR wavelength (780–2500 nm) regions to measure the optical absorption and emission from the sample. Performing such absorption or emission measurements using a fiberscope requires addressing many of the same problems as encountered in performing Raman imaging. The ability to perform combinations of these optical measurements and chemical imaging in the same fiberscope system is also an advantage in that enabling different chemical imaging technologies in one platform provides valuable complementary information.

One problem in performing chemical analysis and chemical imaging in the human body, such as in for example, in the cardio-vascular system or body cavities during, for example, endoscopic surgery, is the occurrence of significant amounts of blood and water at the sample site which both scatters and absorb light in certain wavelength ranges. Further, the positioning of a fiberscope probe to perform an in vivo optical analysis requires accurate steering and viewing thru these body fluids so as to define regions of interest and accurately position the optical probe at the region to be sampled. Viewing more than a few millimeters through blood requires observation at NIR wavelengths. However, such NIR wavelengths are poorly suited for performing Raman scattering or fluorescence measurements.

For example, identification and characterization of vulnerable plaque in the cardio-vascular system is critically related to Cardio vascular disease which is a leading cause of deaths in the United Stated. The in vivo identification and characterization of plaques in the cardio vascular system requires locating the suspect regions and positioning a sampling probe to analyze these regions. Other current methods for characterizing vulnerable plaque such as Intra Vascular UltraSound (IVUS) and thermometry (e.g., Volcano Therapuetics, Inc.) map out some physical properties of the arterial walls to suggest likely areas of plaques, but are not chemically specific and cannot provide any detailed analytical information regarding the chemical state or molecular composition of these target areas or plaques. Optical imaging to position a chemical probe in vivo is desirable but problematic and limited due to the scattering and absorption properties of blood. While certain optical wavelengths in the NIR are known to be more favorable than others for in vivo viewing of the cardiovascular system, these wavelengths are not well-suitable for performing highly specific chemical analysis. For example, the Raman scattering cross sections at longer wavelengths (e.g., NIR) are reduced from VIS wavelength excitation by the fourth power of their respective frequencies. The low cost, high sensitivity Si charge-coupled detectors ("CCD") used for Raman Chemical imaging also have reduced sensitivity for longer wavelength Raman scattered peaks thereby making it difficult to detect the very important CH-bond vibrational region.

Thus, there is a need for an apparatus and method to enable long range viewing, steering and targeting which is optimal in the NIR as well as subsequent and/or simultaneous chemical imaging of the target area which is optimal in the visible range. This invention addresses that need.

SUMMARY OF THE DISCLOSURE

In one embodiment, the disclosure relates to a chemical imaging fiberscope for imaging and collecting optical spectra from a sample comprising at least one illumination fiber for transmitting light from a first and a second light source to a distal end of a fiberscope; a dichroic mirror disposed at said distal end of the fiberscope such that light from said first light source passes substantially straight through said mirror and light of a predetermined wavelength from said second light source is substantially reflected by said mirror toward said sample to thereby illuminate said sample; and at least one collection fiber for receiving light from said illuminated sample and transmitting the received light to an optical device.

In another embodiment, the disclosure relates to a system for imaging and collecting optical spectra from a sample comprising a near infrared ("NIR") light source; a laser light source; a fiberscope including at least one illumination fiber; a dichroic mirror; at least one collection fiber; and an optical device, wherein said at least one illumination fiber is operatively connected at a proximate end to said NIR light source and said laser light source so as to transmit light from said light sources to said dichroic mirror disposed in proximity to a distal end of said illumination fiber and wherein said dichroic mirror allows light from said NIR light source to pass substantially straight through said mirror and substantially reflects light from said laser light source toward said sample to thereby illuminate said sample. The at least one collection fiber can receive light from said illuminated sample and transmit the received light to the optical device for imaging and collecting optical spectra and chemical images of the sample.

In still another embodiment, the disclosure relates to a method of imaging and collecting optical spectra from a sample, the method comprising the steps of providing a fiberscope including at least one illumination fiber operatively connected at a proximal end to a first light source and a second light source so as to transmit light from said first and second light sources to a dichroic mirror disposed in proximity to a distal end of the fiberscope; at least one collection fiber for receiving light from said illuminated sample and transmitting the received light to an optical device; and a dichroic mirror disposed at the distal end of the fiberscope which allows light from the first light source to pass substantially straight through the mirror while substantially reflecting light from the second light source toward the sample to thereby illuminate the sample.

DETAILED DESCRIPTION

The Raman chemical imaging fiberscope combines in a single platform a laser beam delivery system to irradiate samples for Raman spectroscopy, an incoherent fiber optic bundle to deliver white light illumination and a coherent fiber bundle suitable for Raman spectral collection, Raman image collection and digital video collection.

Figure 1:
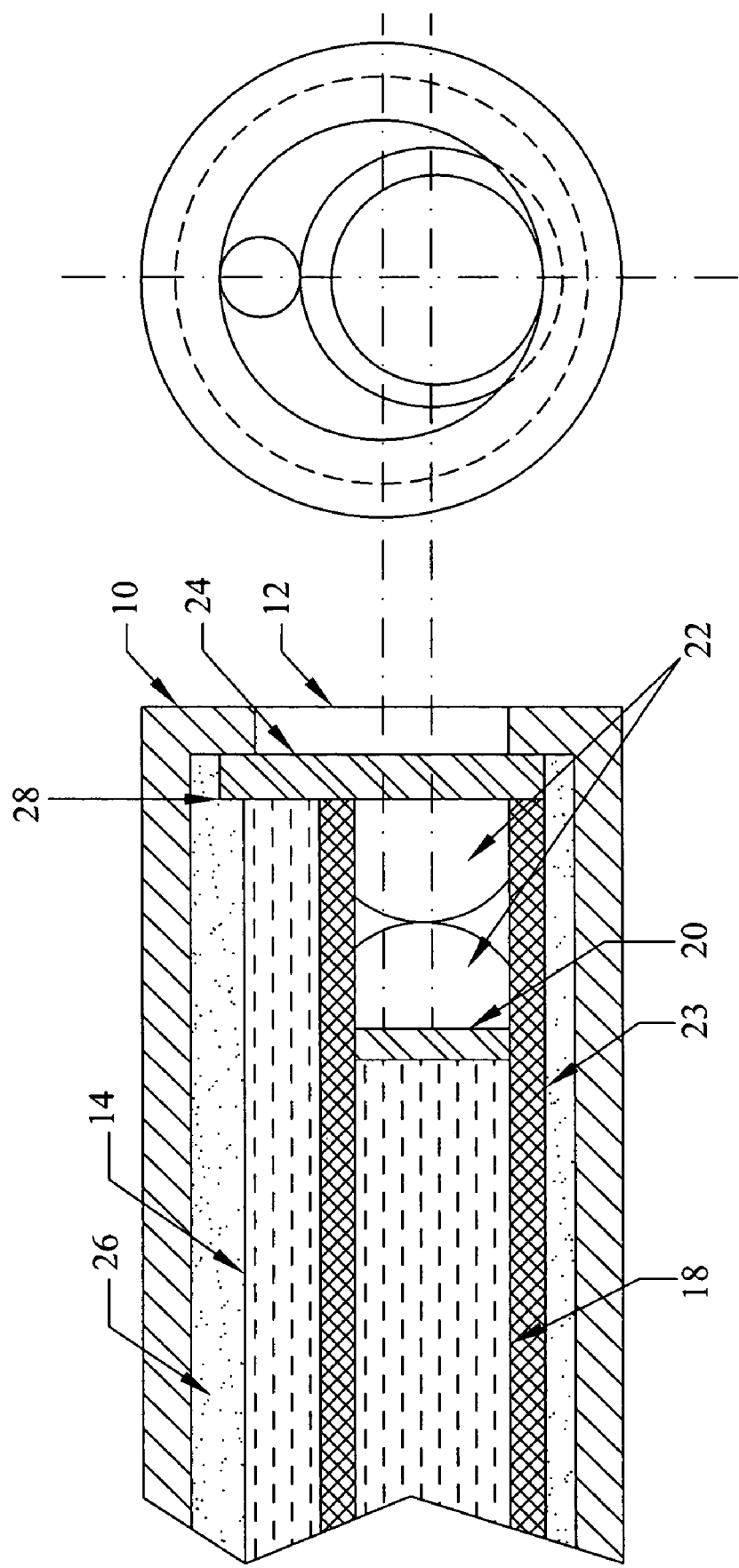
FIG. 1 shows a cross-section of the distal end of the Raman chemical imaging fiberscope.

The distal end of the fiberscope is shown in cross-section in FIG. 1. The external housing 10 surrounds the inner core of the fiberscope. The outer jacket 10 is mechanically rugged and immune to hostile sampling environments. The compression tube 23 holds the fibers 18, the filter 24 and lens 22 in alignment. At the distal end of the fiberscope is window 12. This window is, in one embodiment, composed of quartz, diamond or sapphire and is used as an optically transparent boundary separating the sample environment from the optical components in the probe. In an alternative embodiment, the other biocompatible material such as plastics, glass or semiconductors can be used for the optically transparent window.

Laser illumination fiber 14 delivers laser illumination to the sample. This light passes through laser bandpass filter 24, which filters out all wavelengths of light other than the specific wavelengths of the laser light transmitted through laser illumination fiber 14. The laser light/sample interaction generates Raman scattering. The scattered light is then collected through the end of the fiberscope. It should be noted that laser bandpass filter 24 is spatially patterned and has optical coatings only on the top portion thereof, such that light exiting laser illumination fiber 14 will be filtered, but scattered light entering the end of the probe will not experience any filtering by laser bandpass filter 24. The portion of laser bandpass filter 24 which receives scattered light form the sample and transmits it to image collection bundle 18 is transparent and performs no filtering function.

After passing, through laser bandpass filter 24, the scattered light is apertured by a spatial filter 28 which acts to restrict the angular field or view of the subsequent optical system. The scattered light is then focused by a pair of lenses 22. The light is then passed through laser reflection filter 20. This filter effectively filters out light having a wavelength identical to the laser light, which was originally transmitted onto the sample through laser illumination fiber 14. After passing through filter 20, the light is transmitted back to the imaging apparatus by the image collection bundle 18.

Successful use of the Raman chemical imaging fiberscope depends on the performance of the spectral filters in humid, elevated-temperature environments. Conventional filters are characterized by the presence of microscale pits and voids. These microstructures absorb water in humid conditions, which cause the thin film matrix to swell and the spectral properties to change, causing the fiber optic probe to be useless. In addition, the coefficients of thermal expansion of traditional dielectric filter thin films (i.e., ZnS or ZnSe) are relatively large. When exposed to elevated temperatures the traditional filter center spectral bandpass shifts, rendering them useless unless a mechanism is devised to rotate the filters and turn them. For example, ZnS has a temperature coefficient of 0.05 nm/° C.

In the preferred embodiment, the filters are metal oxide dielectric filters. Metal oxide filters have low coefficients of thermal expansion and when exposed to elevated temperature environments the thin film materials comprising the Fabry-Perot cavities do not exhibit gross variation in thin film thickness. As a consequence, the metal oxide filters are insensitive to temperature induced spectral changes, primarily peak transmittance. In addition, the metal oxide thin film coating is also insensitive to humidity which enhances the filter performance when exposed to hostile conditions. The metal oxide filters employ $SiO_2$ as the thin film material, which exhibits a temperature dependent spectral band shift coefficient of about 0.005 nm/° C.

The imaging fiber optic bundles are preferably high temperature resistant coherent fiber optic bundles, such as those developed by Schott Glass. These bundles have the unique property that the polyamide cladding employed for typical coherent fiber bundles is leached away (in acid bath) leaving an all-glass fiber bundle that is flexible and can be operated at high temperatures up to about 400° C.

Video imaging of the sample is performed by shining white light on the sample. The white light is transmitted via fibers 26. High quality imaging optics are employed to provide the ability to visually inspect the sample area and to obtain Raman chemical images. Collection lenses 22 focus an image of the sample on the image collection bundle 18. The coherent image collection bundle 18 independently captures white light and Raman scattered photons from the sample surface. The Raman chemical imaging fiberscope provides remote real-time video imaging of the sample when the white light is directed through the image collection bundle 18 to a video CCD. Live video capability assists insertion of the fiberscope and allows Visual inspection of the sample area in preparation for spectroscopic analysis. White light for video imaging can be produced by a high power (300 W) Xe lamp.

Figure 2:
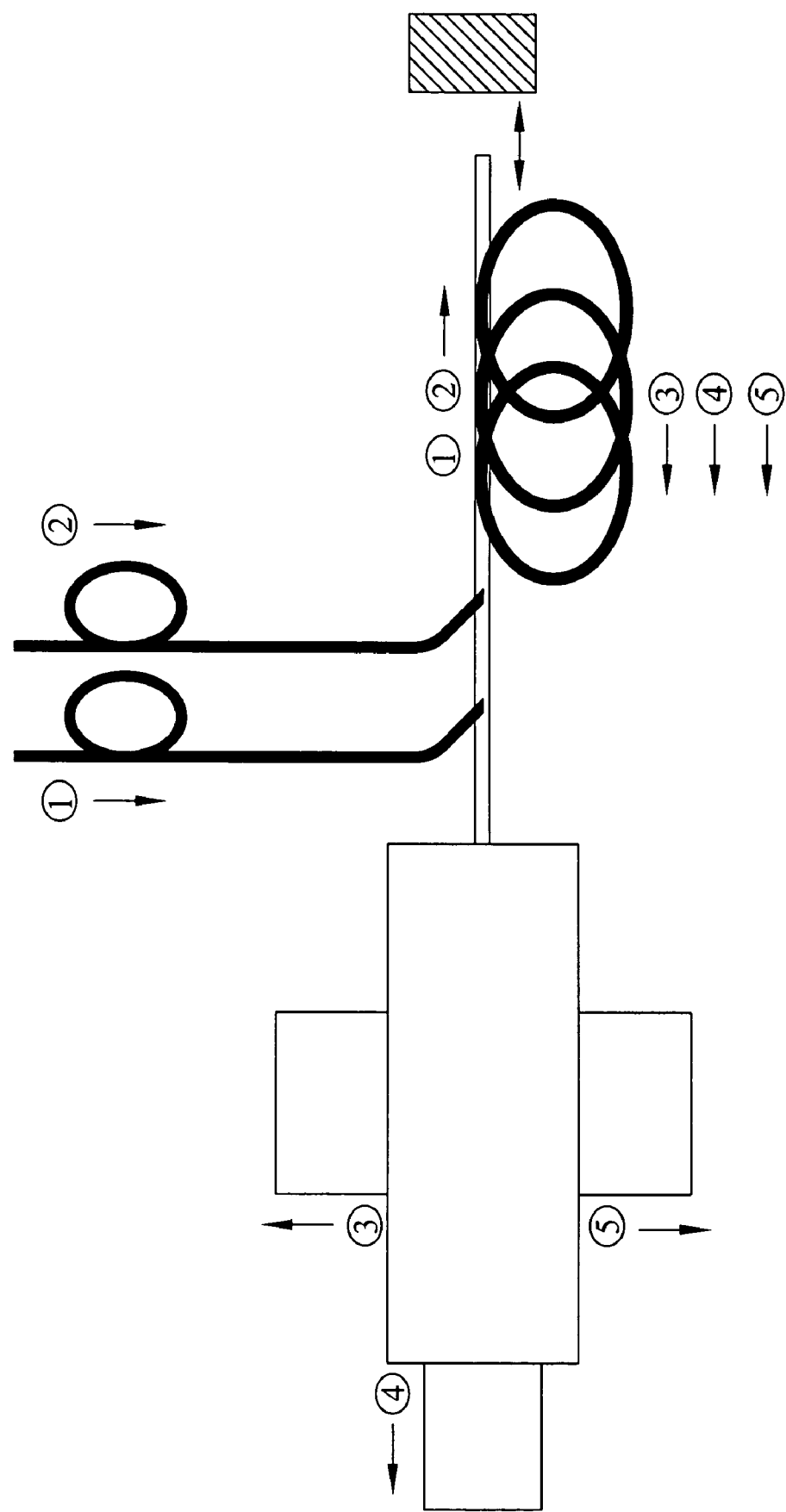
FIG. 2 shows a functional flowchart of pathways for light delivery and collection through the chemical imaging fiberscope.

The Raman scatter is collected through the coherent image collection bundle 18 used to capture the live video. However, laser rejection filter 20 is used to suppress generation of $SiO_2$ Raman background within the image collection bundle 18. As shown in FIG. 2, once collected, the Raman scatter can be diverted in two directions. When sent to a dispersive spectrometer, the Raman chemical imaging fiberscope provides conventional Raman spectral information. The Raman scatter can also be directed through a liquid crystal tunable filter (LCTF) imaging spectrometer onto sensitive digital CCD. Because the Raman image is maintained through the image collection bundle 18, high quality Raman chemical images can be collected across the fiberscope field of view.

FIG. 2 shows a functional diagram of the Raman chemical imaging fiberscope system. Laser light illumination and white light video illuminations are represented by reference numbers 1 and 2 respectively. These lights enter the fiberscope and are transmitted out the end of the scope to the sample. The Raman spectrum 3, the Raman image 4 and the live video image 5 are transmitted back into the end of the fiberscope. Raman spectrum 3 and Raman image 4 are delivered to processing apparatus which effectively displays the desired information, as described above, while live video image 5 is directed to a monitor for viewing by the user.

Figure 3A:
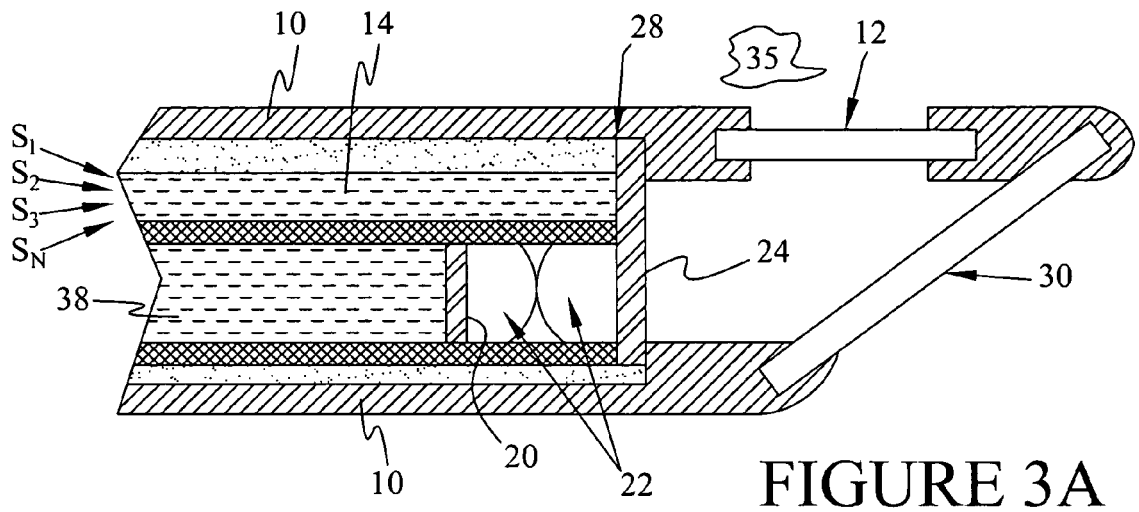
FIG. 3A is a schematic representation of one embodiment of the disclosure.

FIG. 3A is a schematic representation according to one embodiment of the disclosure. Referring to FIG. 3A, a system is shown having illumination fibers 14 receiving photons from various sources identified as $S_1, S_2, S_3 \ldots S_n$. For example, the first light source can be a near infrared (NIR or broadband NIR) while second and third light sources, respectively, can be laser and/or white light. The white light can be visible VIS (broadband) or ultraviolet UV (broadband). The NIR source can have a wavelength in the range of about 780–2500 nm or 0.78–2.5 μm. In one embodiment, the exemplary apparatus of FIG. 3A may include a switch (not shown) for alternately connecting any of the sources ($S_1 \ldots S_n$) to the at least one of the illumination fibers 14. For example, the switch can connect the first light source to one of the illumination fibers 14 for guiding the fiberscope through for example an artery to the sampling position. The switch can also connect the second light source to another of illumination fiber 14 for simultaneously or sequentially illuminating the sample or performing spectroscopy.

Illumination fibers 14 can comprise one or more transparent optical fibers devised to transmit light from one or more sources to sample 35. In one embodiment, plural illumination fibers can be arranged as a bundle such that one of the illumination fibers 14 transmits light exclusively from a first light source to the sample while another of the plural illumination fibers transmits light exclusively from a second light source to the sample. According to still another embodiment, illumination fibers 14 and light sources ($S_1 \ldots S_n$) can be arranged such that at least one illumination fiber 14 transmits light from the first, second and third light sources to the distal end of the fiber scope. Illumination fibers 14 can include conventional transparent optical fibers.

Interposed between the distal end of the illumination fibers 14 and sample 35 is dichroic mirror 30. The dichroic mirror can be selected to reflect light of predetermined wavelength while allowing light of other wavelengths to pass substantially through mirror 30. In other words, in one embodiment dichroic mirror 30 is positioned at the distal end of the fiberscope such that light from a first light source passes substantially through the mirror while light of a predetermined wavelength (for example, from the second light source) is substantially reflected by the mirror toward the sample in order to illuminate sample 35. While the exemplary embodiment of FIG. 3A shows dichroic mirror 30 positioned at an angle with respect to housing 10 of the fiberscope, the principles of the disclosure are not limited thereto. The dichroic mirror 30 can be selected such that its optical properties would be resistant to temperature and/or humidity changes.

In one embodiment, the predetermined wavelength can be about 670 nm. The predetermined wavelength can also be in the range of about 220–1500 nm, 500–850 nm or 270–550 nm.

Photons emitted from sample 35 can be collected through collection fibers 38 and transmitted through one or more spatial filter 28 to an optical device (not shown). It should be noted that laser bandpass filter 24 is spatially patterned and has optical coatings only on the top portion thereof, such that light going into the fibers 38 is not filtered. Spatial aperture 28, lens 22 and spectral filter 20 are interposed between sample 35 and collection fibers 38. Spatial filter 28 can be used to reduce unwanted light from entering the fibers 38. Lens 22 can focus light into collection fibers 38. Spectral filter 20 can be any conventional bandpass filter capable of rejecting light of an unwanted wavelength. Filters 20 can be configured such that the photons received by collection fibers 38 can have a wavelength in the range of about 500 to 680 micrometers. In one embodiment, spectral filter 20 is used to reject light having a wavelength substantially similar to the wavelength of the light emitted by the laser light source while allowing lights having a different wavelength to pass through.

Lens 22 are also interposed between sample 35 and collection fibers 38. Lens 22 can be a conventional optical lens for gathering and/or focusing light. While the exemplary configuration of FIG. 3A shows a particular order and arrangement for spatial filter 28, spectral filters 24 and 20 and lens 22, the principles of the disclosure are not limited thereto. For example, a plurality of optical devices can be assembled to function as a spatial or spectral filter. Moreover, the utilization of each and all of these elements is optional and may not be necessary for a desired outcome.

In one embodiment of the disclosure photons scattered, reflected, refracted or fluoresced by sample 35 are transmitted by collection fibers 38 to an optical device (not shown). The optical device can be selected according to a desired application for the system. For example, the optical device can be a Raman chemical imaging spectrometer and detector. The optical device can be further coupled to a controller, a display device or a recording medium.

The exemplary system shown in FIG. 3A also includes external housing 10 having window 12 at its distal end. Window 12 may include quartz, diamond or sapphire. In some cases window 12 may also include plastic, glass or a semiconductor. In another embodiment, window 12 may include a first portion which is spatially patterned for the light from said first light source and a second portion which is transparent for the light from the second source.

In an exemplary application, the fiberscope of FIG. 3A can be configured for collecting Raman spectra from a sample by using NIR as $S_1$, a laser light as $S_2$ and white light as $S_3$. The fiberscope can include at least one illuminator fiber, a dichroic mirror 30, a collection fiber bundle 38 and an optical device (not shown). The illumination fiber 32 can be optically coupled, at a proximal end, to $S_1$ and $S_2$ so as to transmit light from the light sources to the dichroic mirror 30 disposed at the distal end of illumination fiber 14. Dichroic mirror 30 can be configured to allow light from $S_1$ to pass substantially straight through the mirror while reflecting light from $S_2$. Collection fibers 38 can receive light from the illuminated sample (e.g., in the form or scattered, reflected, refracted or fluoresced photons) and transmit the received photons to the optical device for imaging and collecting Raman spectra of the sample. Spectral filter 20 can be disposed between the sample 35 and collection fibers 38 for rejecting light having wavelength similar to $S_2$. In addition, spatial filter 28 can be disposed between sample 35 and collection fibers 38 to control the angular field of view of collection fibers 38.

In FIG. 3A a single dichroic mirror 30 provides the illumination and viewing of forward objects for wavelengths above $\lambda_1$ (e.g., NIR). For illuminating wavelengths below $\lambda_1$, the reflection from dichroic mirror 30 occurs onto the sample 35. Light scattered, absorbed or emitted from the sample 35 from this illumination can be reflected by dichroic mirror 30 into the filters 28 and 20 as well as lens 22, the filter 24 and the collection fiber bundle 38 to the optical analysis and ultimately the detection system (not show).

Figure 3B:
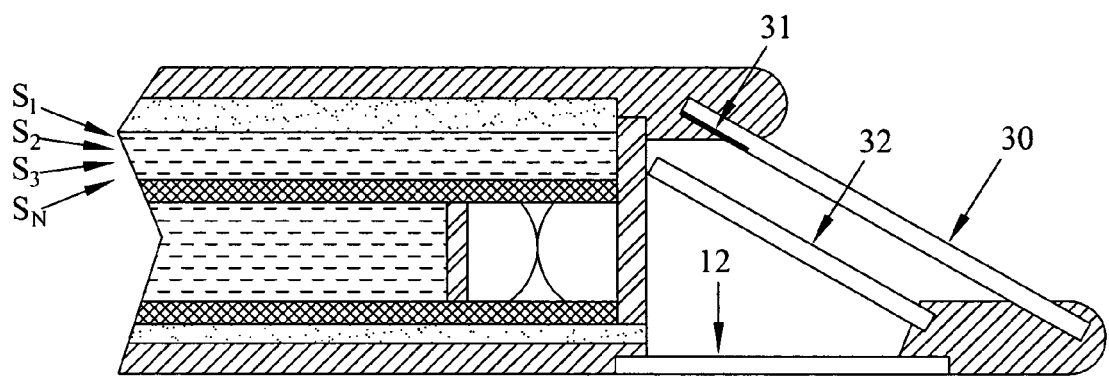
FIG. 3B is a schematic representation of another embodiment of the fiberscope's dichroic probe region.

FIG. 3B is a schematic representation of another embodiment of the fiberscope's dichroic probe region. The schematic representations of FIGS. 3A and 3b utilize discrete optical flats or plates for the dichroic mirror 30, 31 and 32 and window 12. In FIG. 3B several dichroic mirrors 30, 31 and 32 are utilized to enable different illumination and sampling applications. This embodiment also illustrates the flexibility that combination of different dichroic mirrors can offer. The dichroic elements at the three different spatial locations can be tailored to operate at different wavelengths. In one configuration dicrhoic element 32 can be removed and a dichroic mirror coating 31 can cover a portion of dichroic mirror 30. Coating 31 can be a dichroic coating that is adopted to be effective for certain wavelengths corresponding to one or more illumination wavelength (e.g., $S_1$ and $S_2$) but not effective for others (e.g., $S_3$ to $S_N$). In an alternative embodiment, element 31 may be a graded dichroic mirror or polychroic mirror having a different reflection and transmission properties with respect to the wavelength transmitted through transmission fibers 14. In still another embodiment, dichroic mirror 30 may be a window to allow viewing under visible light. Alternatively, it may be a dichroic mirror to allow viewing under NIR radiation. Similarly, secondary dichroic mirror 32 can be an additional mirror or a dichroic mirror depending on the intended application. For NIR imaging, secondary mirror 32 can be have dichroic surfaces on both sides to reflect NIR light for viewing/steering and transmits VIS or UV light for Raman, VIS or Fluorescence spectroscopy.

Figure 3C:
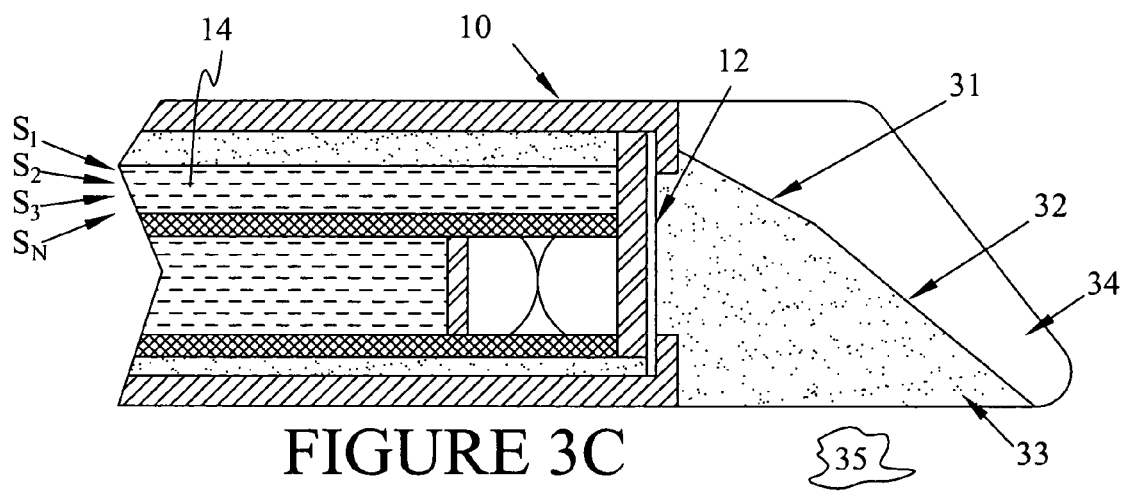
FIG. 3C is a schematic representation of another embodiment of the fiberscope's dichroic probe region.

FIG. 3C is a schematic representation of another embodiment of the fiberscope's dichroic probe region. Particularly, FIG. 3C shows a compound optical element composed of optical material 33 and 34 and dichroic mirror surfaces 31 and 32. Dichroic mirrors 31 and 32 can be made from the same contiguous material or they can be made from two separate segments. In the exemplary embodiment of FIG. 3C, the incident and scattered radiations are reflected from the same dichroic mirror. In one embodiment, the forward viewing is optimized by tilting fibers 14 downward toward the most extended region of material 33 (not shown) in order to direct illumination closer to the center of the dichroic mirror 30.

The exemplary embodiment represented in FIG. 3C includes composite optical material that are fused together to form an internal dichroic mirror surface. The composite optical material include high quality spectroscopic grade optical material 33, such as, for example quartz, which is highly uniform and lacks defects that may scatter or absorb fluoresce in the UV, VIS, or NIR regions. This allows uniform transmission of light of wavelengths in a region of interest for spectroscopy or chemical imaging. The composite optical material may also include capping material 34 which transmits light having VIS and NIR wavelengths but need not be spectroscopic quality material. The capping material 34 may be biocompatible and clearly transmit light in the VIS and/or NIR thereby enabling visual image formation. The composite structure can function similar to FIG. 3B. The dichroic surface 31 can provide illumination and viewing of forward objects having wavelengths above $\lambda_1$ (for example, in the NIR). For illuminating wavelengths below $\lambda_1$, reflection from 31 occurs onto the sample 35. Light scattered, absorbed or emitted from sample 35 may be reflected by the dichroic mirror surface 32 into filters 22, 24, 28 and lens 36. The light is then received by collection fiber 38 and directed to the optical devices (not shown) for analysis and detection.

One advantage of a compound optical element as shown in FIG. 3C is its simplicity of fabrication and mounting. For example, the opening at the distal end of the fiberscope body 10 and the proximal end of compound dichroic element can be tapped so as to snap into the fiberscope body housing 10. The application of a refractive matching fluid atop of the fiberscope window 12 before insertion of the compound lens not only provides a refractive index matched interface but acts as a seal to prohibit bodily fluids from entering this interface. Such a snap-in, composite dichroic lens can be readily replaced in the field.

Figure 4:
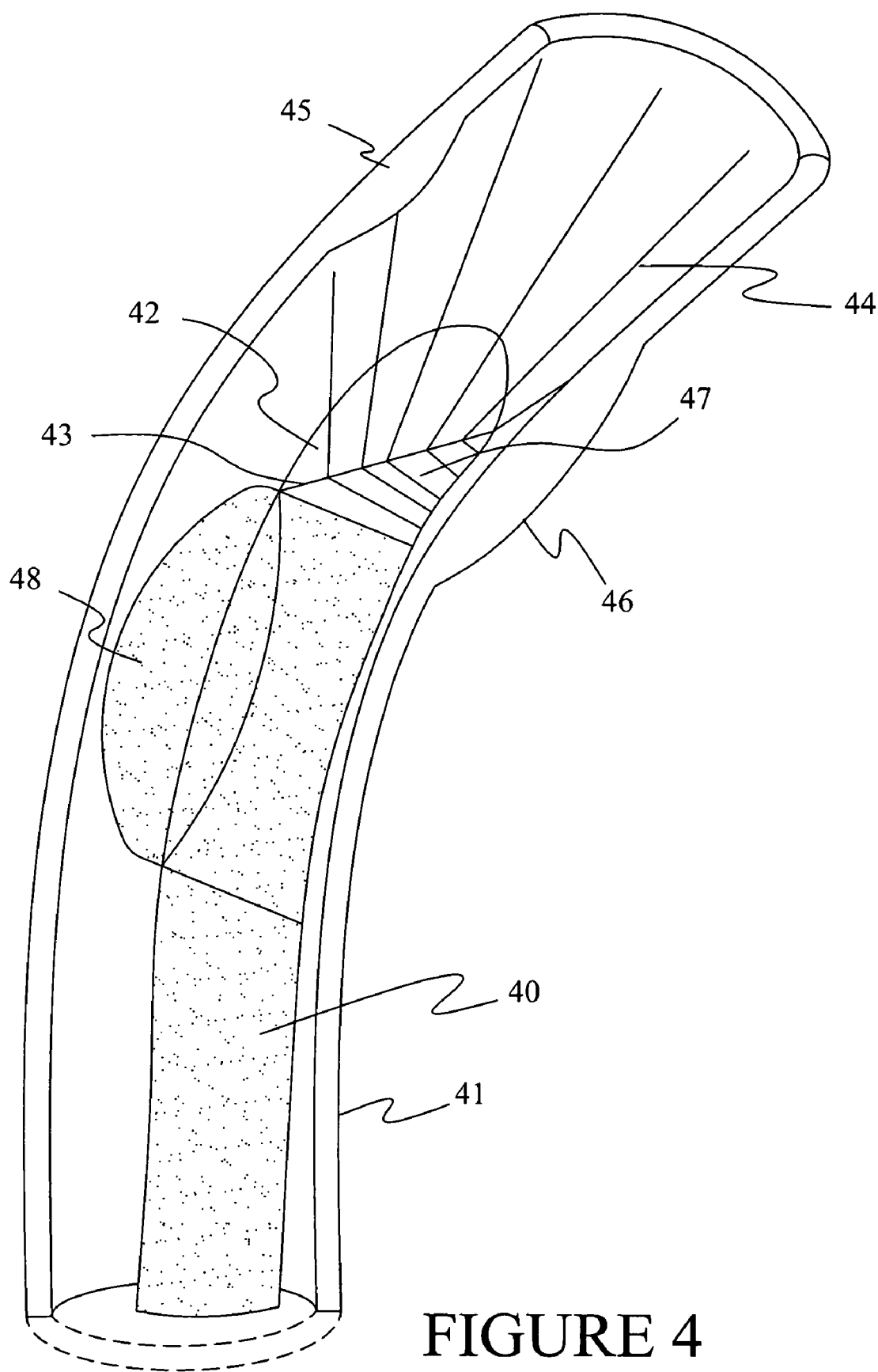
FIG. 4 is a schematic representation of a dichroic fiberscope probe in an artery according to one embodiment of the disclosure for evaluating regions in the arterial wall.

FIG. 4 is a schematic representation of a dichroic fiberscope probe in an artery according to one embodiment of the disclosure for evaluating regions in the arterial wall. More specifically, FIG. 4 shows fiberscope 40 inside a body lumen (an artery) 41. In the exemplary embodiment of FIG. 4, fiberscope 40 also includes composite optical element 42 having dichroic mirror 43. Light having NIR wavelengths (shown as rays 44) originate from source 33 from the composite optical element 42 for illuminating objects in the arterial wall 45. After defining a suspicious area such as plaque 45 or area 46, the head of the fiberscope and the composite optical element can be positioned at or near such area. As shown in FIG. 4, the probe is positioned for detailed spectroscopic examination of target area 46. Once positioned, spectroscopy at a second wavelength can be performed 47 to further diagnose the target area. To minimize the interference from blood and other bodily fluids, an inflatable balloon 48 can be inflated to push the composite optical element into the target region so as to temporarily squeeze out residual blood or bodily fluids. Such balloons are frequently used in cardio vascular devices and can be incorporated herein to enhance inspection and add functionality. Spectroscopy can be performed using rays 44 that have been reflected off the dichroic mirror 43 onto the target region 46. Scattered, absorbed or fluoresced light from target region 46 is reflected off dichroic mirror 43 into the spectroscopic fibers 38 (see FIG. 3A).

FIG. 54 shows the imaging capabilities of the Raman chemical imaging fiberscope. FIGS. 4A and 4B show a high fidelity image of the exterior and interior of a bore hole, respectively. These are bright field images using white light illumination which show the video performance of the Raman chemical imaging fiberscope. Overall, the Raman chemical imaging fiberscope has a wide field of view and superb image quality.

The video performance of the Raman chemical imaging fiberscope was evaluated by recording a digital image of a USAF 1951 resolution target. The target was illuminated with a diffuse Xe arc lamp source. The output of the Raman chemical imaging fiberscope was optically coupled to a color CCD video camera and bright field images were digitized using a digital frame grabber. To determine the laser spot position and dimension a diode pumped Nd:YVO$_4$ laser—doubled to produce 532 nm light—was injected into the laser delivery fiber. The resultant laser spot was projected onto the resolution target substrate at a nominal working distance of 1 cm.

Figure 5:
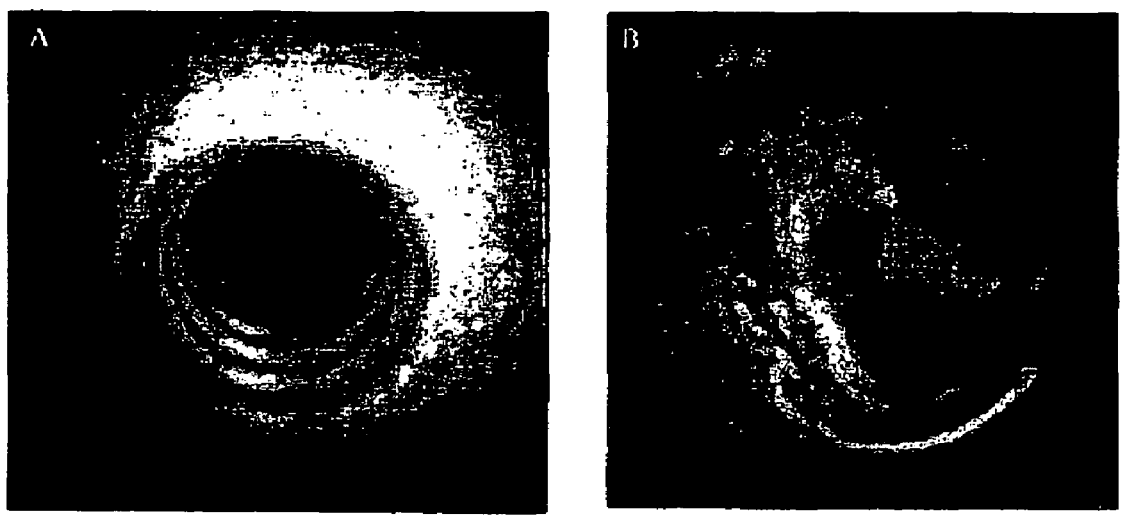
FIGS. 5A and B respectively show the bright field images of the exterior and interior of a bore hole captured through the chemical imaging fiberscope.
Figure 6:
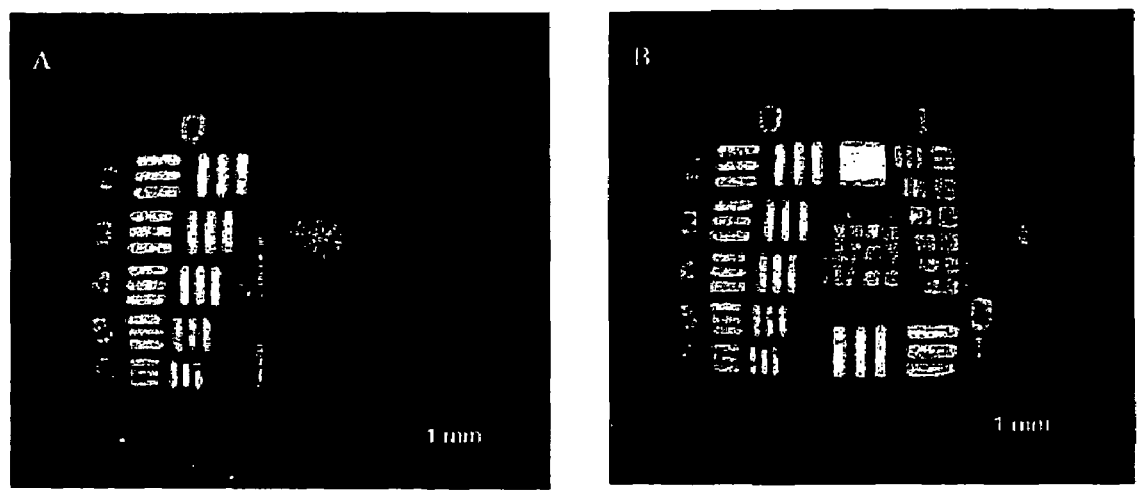
FIG. 6A shows an image of the laser beam projected onto a resolution target images collected through the chemical imaging fiberscope.
FIG. 6B shows an image of the resolution target only for comparison.

FIG. 5 shows resolution target imaged collected through the Raman chemical imaging fiberscope when back-illuminated with a diffuse Xe source. In FIG. 5A a 532 nm laser beam was focused into the laser delivery fiber using a high efficiency laser to fiber optic coupler and an image of the laser spot was recorded on a diffuse target super imposed on the resolution target. At a working distance of 1 cm the spot seen near the center of the target image is approximately 2.5 mm in diameter. The laser spot size can be controlled through laser to fiber optic injection strategies and via working distance to the sample. For comparison, FIG. 5B shows the digital image of the USAF resolution target.

As previously described, high performance, environmentally resistant spectral filters can be incorporated into the distal end of the flexible Raman chemical imaging fiberscope. Room temperature spectra were acquired to measure the out of band rejection efficiency of the fiberscope using combinations of white light and laser light. Room temperature spectra were acquired to measure the 532 nm laser rejection efficiency during fiberscope collection. Laser rejection is required for the observation of the weak Raman signal and to prevent the inherent Raman scatter of the collection fiber. Xenon light was sent into the collection end of the fiberscope. The output from the viewing end of the fiberscope was measured using a dispersive spectrometer.

Figure 7:
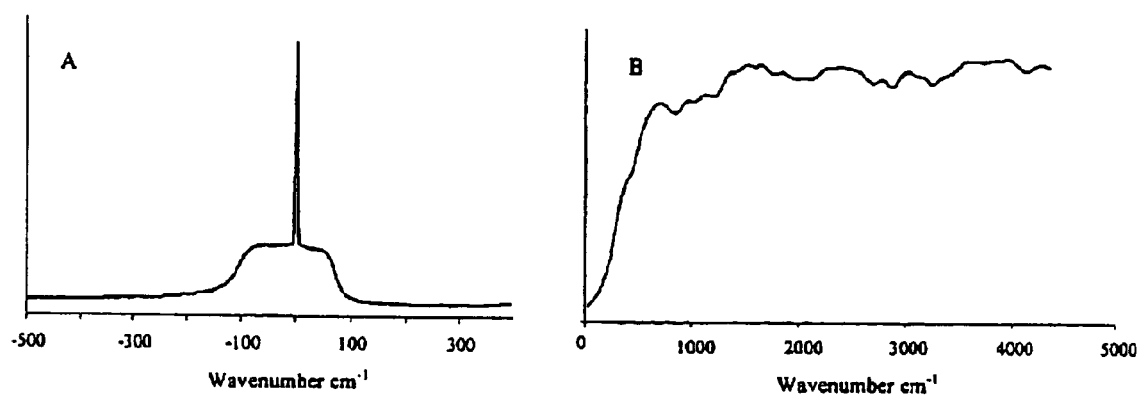
FIG. 7A shows the simultaneous transmission of white light and laser light through the laser delivery fiber optic and laser bandpass filter.
FIG. 7B shows the transmission bandpass through the laser rejection filter and coherent imaging bundle.

FIG. 7 shows transmission spectra collected through the Raman chemical imaging fiberscope. Specifically, FIG. 7A shows the transmission bandpass through the laser deliver fiber optic under simultaneous Xe white light and 532 nm laser light illumination. From this spectrum, it is apparent that the incorporated bandpass filter sufficiently passes 532 nm light while cutting off transmission above 140 cm$^{-1}$ red-shifted from the laser line. FIG. 7B shows the transmission bandpass through the filter incorporated within the coherent fiber bundle. It is apparent that the incorporated notch filter sufficiently rejects 532 nm light while passing light above 200 cm$^{-1}$ red-shifted from the laser line.

Figure 8:
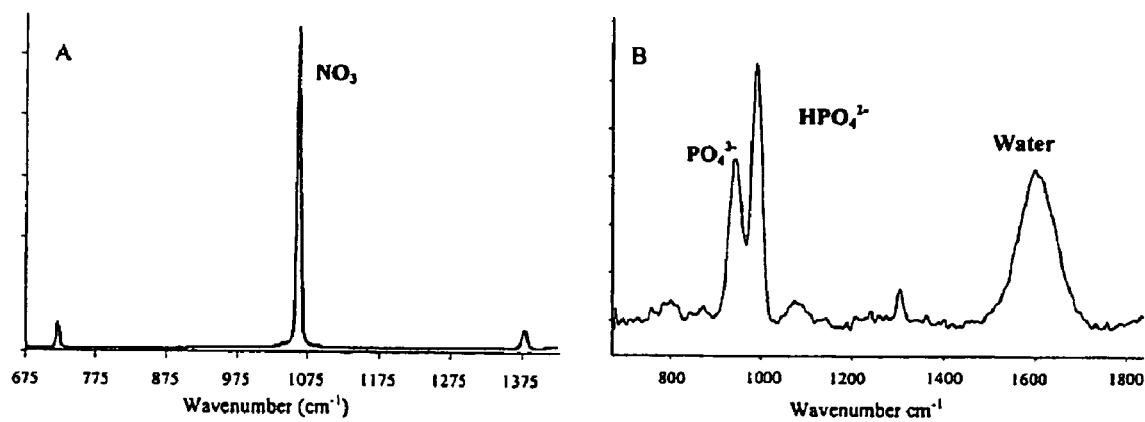
FIGS. 8A and B show Raman spectra of a sodium nitride pellet and a sodium phosphate solution, respectively, captured through the chemical imaging fiberscope.

Dispersive Raman spectra of sodium nitrate and sodium phosphate in aqueous solution collected with the Raman chemical imaging fiberscope are presented in FIG. 8. The sodium nitrate Raman spectrum in FIG. 8A reveals the characteristic nitrate band at 1065 cm$^{-1}$. Note the high signal to background ratio (S/B) and the absence of fiber optic Raman background. In FIG. 8B, the phosphate bands, at 945–995 cm$^{-1}$ can be seen.

Room temperature Raman spectra of a sodium nitrate pellet was collected to assess the Raman collection performance of the Raman chemical imaging fiberscope. The viewing end of the fiberscope was coupled to a dispersive Raman spectrometer. Illumination of the sodium nitrate pellet was provided by injecting laser light into the laser delivery fiber.

High temperature Raman spectra of zirconium oxide were also collected. A furnace was used to heat the sample and digital end of the Raman chemical imaging fiberscope. A thermocouple was used to monitor the temperature at the distal end of the fiberscope. A viewing end of the fiberscope was coupled to a dispersive spectrometer. Illumination of the zirconium oxide pellet was provided by injecting laser light into the laser delivery fiber of the Raman chemical imaging fiberscope.

Figure 9:
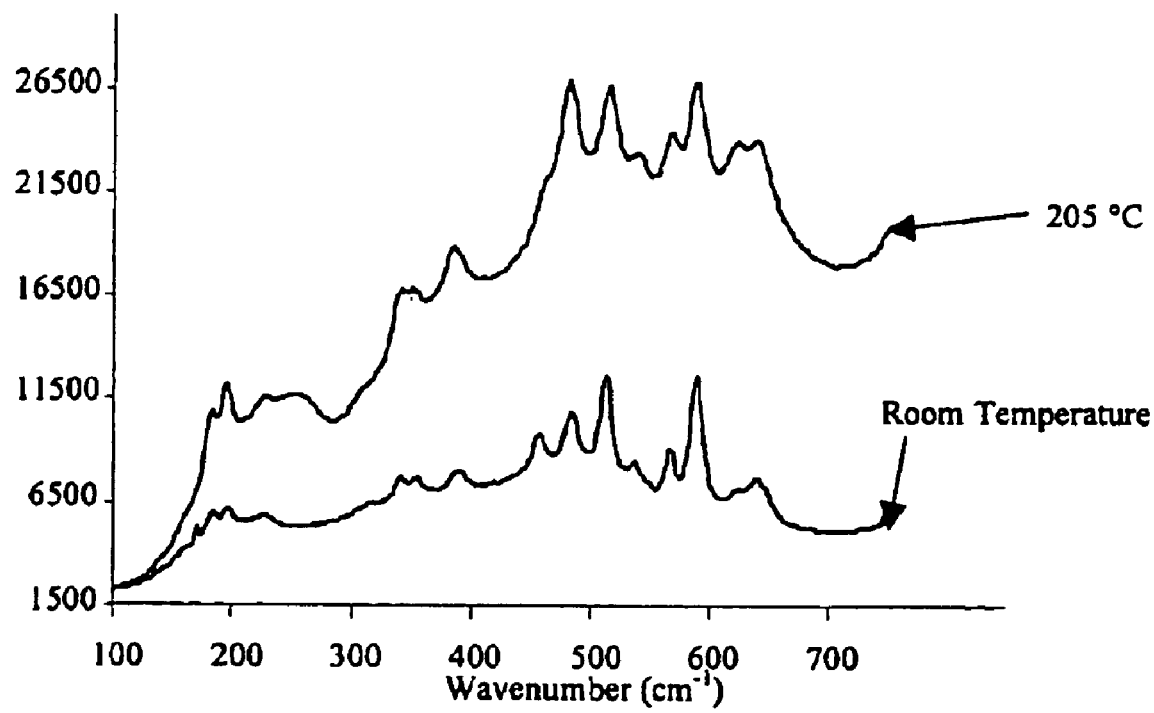
FIG. 9 shows Raman spectra of zirconium oxide collected at room temperature and at 205° C. through the chemical imaging fiberscope according to one embodiment of the disclosure.

FIG. 9 shows two zirconium oxide spectra collected (1) at room temperature (i.e., 27° C.) and, (2) at the elevated temperature of 205° C. The Raman features are still discernable in the high temperature spectrum. There is an increase in the overall intensity of the background signal (thermal background) and in the relative intensities of the peaks. It is noted that both spectra show Raman features to well within 200 cm$^{-1}$ of the laser line.

Raman chemical image data was collected from an over the counter pharmaceutical tablet containing aspirin (Alka Seltzer from Bayer® Corp.). The image from the viewing end of the fiberscope was focused onto a CCD camera and an LCTF was inserted into the optical path. Dispersive spectroscopy revealed that the tablet excipient had a Raman band at 1060 cm$^{-1}$. Since this is close to the 1044 cm$^{-1}$ Raman band of aspirin, these two peaks were used for chemical image analysis. A CCD image was collected every 9 cm$^{-1}$ while the LCTF was tuned form 1000 cm$^{-1}$ to 1110 cm$^{-1}$.

Figure 10:
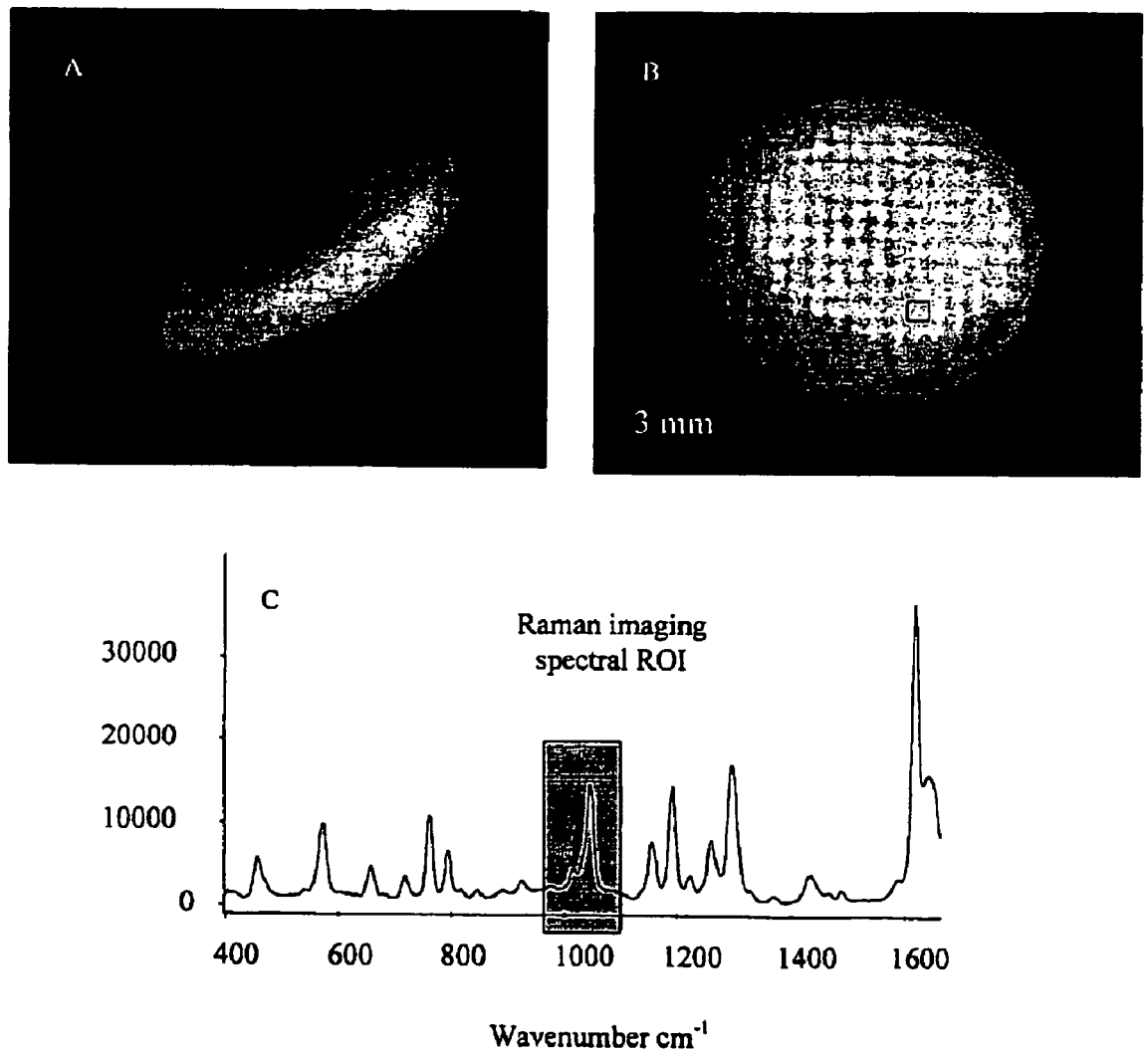
FIGS. 10A and 10B show bright field images of an aspirin tablet collected through the fiberscope under white illumination conditions.
FIG. 10C shows a Raman spectrum of the aspirin tablet captured from the boxed region in FIG. 9B and collected with a dispersive Raman spectrometer under Raman spectroscopy conditions.

Images of the tablet collected through the fiberscope using ambient light can be seen in FIGS. 10A and 10B. The box in FIG. 10B shows the region from where the Raman spectrum in FIG. 10C was acquired. FIG. 10C shows a dispersive Raman spectrum dominated by aspirin (acetylsalicylic acid). The box shaded in gray represents the spectral range that was sampled to generate Raman chemical images.

The multivariate technique cosine correlation analysis ("CCA") was applied to Raman chemical image data using a ChemImage software. CCA is a multivariate image analysis technique that assesses similarity in chemical image data sets while simultaneously suppressing background effects when performed in conjunction with normalization of each linearly independent Raman spectra contained in the image dataset. CCA assesses chemical heterogeneity without the need for extensive training sets. CCA identifies differences in spectral shape and effectively provides molecular-specific contrast that is independent of absolute intensity.

Figure 11:
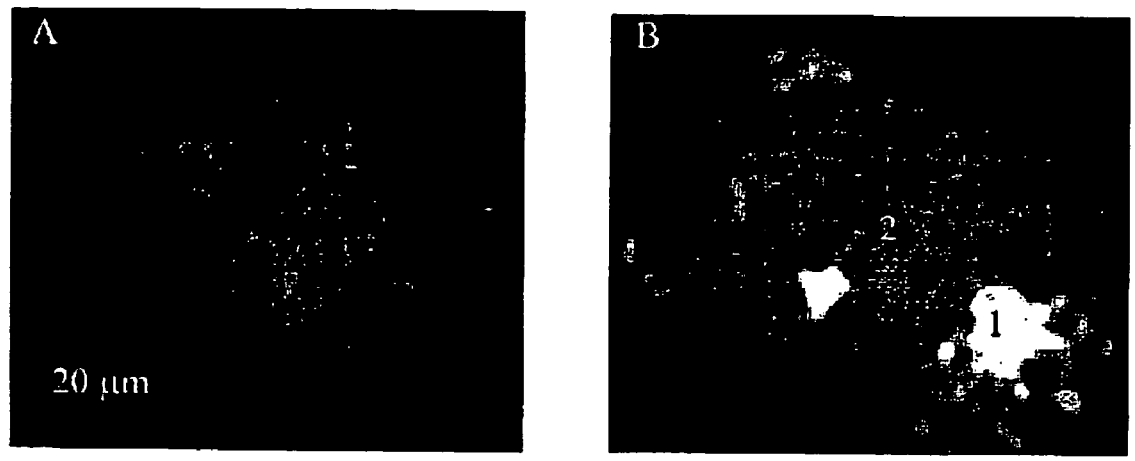
FIG. 11A shows bright field images of a micro region of a tablet containing aspirin collected through the fiberscope under white light illumination conditions.
FIG. 11B shows a Raman chemical image of the same tablet collected through the fiberscope operating under Raman imaging conditions.
FIG. 11C shows representative Raman spectra collected through imaging spectrometer of aspirin and excipients.
Figure 11:
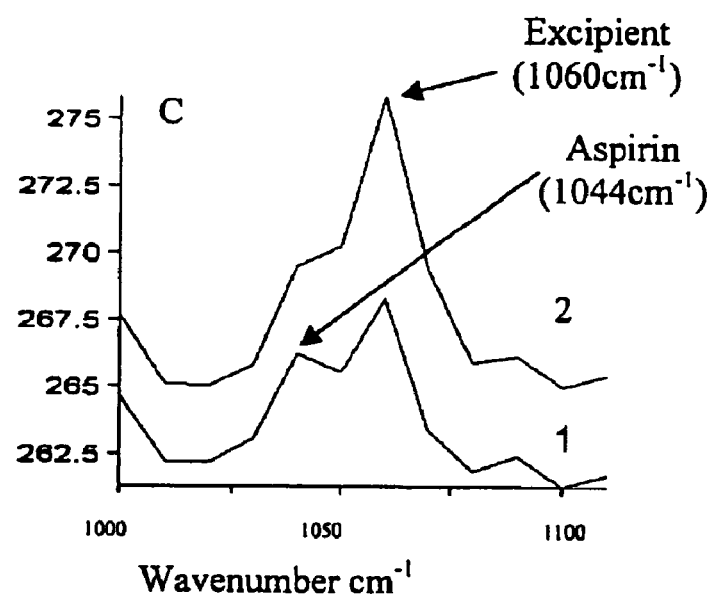

FIG. 11 displays the Raman chemical imaging results from the aspirin tablet. Specifically, FIG. 11A is a bright field image of the sampled area captured through the Raman chemical imaging fiberscope. FIG. 11B is a grayscale Raman chemical image generated using CCA with the brightest regions showing the aspirin component at 1044 cm$^{-1}$ and the darker regions showing the excipient component (calcium carbonate) collected at 1060 cm$^{-1}$. FIG. 11C shows LCTF Raman spectra from regions 1 (localized aspirin) and 2 (excipient), respectively.

The Raman chemical imaging fiberscope is capable of, among others, the following: laser delivery, white light illumination, video collection, Raman spectral collection and LCTF-based Raman chemical imaging capability within a compact device (the distal end outside diameter of the flexible fiberscope is only 2 mm). The Raman chemical imaging fiberscope is environmental resistant and can be used in a variety of hostile and confined environments over a range of operating temperatures and humidity. Due to its compact dimensions and rugged design, the Raman chemical imaging fiberscope is well suited to in situ industrial monitoring and in vivo clinical applications.

Although the disclosure has been described in the context of a Raman fiberscope probe using Raman scattered light, the principles disclosed herein offer the ability to perform other chemical or spectroscopic imaging techniques such as near infrared, fluorescence or luminescence chemical imaging. For example, while Raman measures scattering and provides molecular based chemical information, absorption of VIS or NIR light over a range of wavelengths also provides an optical chemical signature which can be used to interpret or differentiate the chemical state of the sample. Using this fiberscope imaging system such optical absorption can be measured by integration over the sample and detected using an appropriate spectrometer or imaged to form a UV, NIR or VIS absorption chemical image using an appropriately designed LCTF and detector. Similarly, light emission arising from, for example, fluorescence can be integrated over the sample and detected with a spectrometer or imaged to form a UV, VIS or NIR emission chemical image using an appropriately designed LCTF and detector.

Although the disclosure was described in the context of a Raman fiberscope probe, the present disclosure offers the ability to perform other chemical (spectroscopic) imaging techniques such as near infra-red and luminescence chemical imaging.

The principles of the disclosure have been described in relation to particular exemplary embodiments which are illustrative not restrictive. Alternative embodiments may become apparent to those skilled in the art to which the present disclosure pertains without departing from the principles disclosed herein.

What is claimed is:

1. A chemical imaging fiberscope for imaging and collecting at least one spectra from a sample comprising:
    at least one illumination fiber for transmitting light from a first and a second light source to a distal end of said fiberscope;
    a dichroic mirror disposed at said distal end of the fiberscope such that light from said first light source passes substantially through said mirror and light of a predetermined wavelength from said second light source is substantially reflected by said mirror toward said sample to thereby illuminate said sample; and
    at least one collection fiber for receiving light from said illuminated sample and transmitting the received light to one or more optical device.

2. The fiberscope of claim 1 including plural illumination fibers wherein at least one of said plural illumination fibers transmits light exclusively from said first light source.

3. The fiberscope of claim 1 further comprising a spectral filter disposed between said sample and said at least one collection fiber so that said predetermined wavelength of light from said second light source is rejected.

4. The fiberscope of claim 3 wherein said predetermined wavelength is approximately 670 nanometers.

5. The fiberscope of claim 3 wherein said predetermined wavelength comprises at least one wavelength each of which is in a range of wavelengths from 220 to 1500 nanometers.

6. The fiberscope of claim 3 wherein said predetermined wavelength comprises at least one wavelength each of which is in a range of wavelengths from 500 to 850 nanometers.

7. The fiberscope of claim 3 wherein said predetermined wavelength comprises at least one wavelength each of which is in a range of wavelengths from 270 to 550 nanometers.

8. The fiberscope of claim 1 wherein said second light source is a laser.

9. The fiberscope of claim 1 wherein said first light source is a broadband near infrared light source.

10. The fiberscope of claim 1 wherein said second light source is a broadband near infrared light source.

11. The fiberscope of claim 1 wherein said second light source is a broadband visible light source.

12. The fiberscope of claim 1 wherein said second light source is a broadband ultraviolet light source.

13. The fiberscope of claim 1 including plural illumination fibers wherein one of said plural illumination fibers transmits light exclusively from said first light source and wherein another of said plural illumination fibers transmits light exclusively from said second light source.

14. The fiberscope of claim 1 including a third light source such that said at least one illumination fiber transmits light from said first, second, and third light sources to said distal end of said fiberscope.

15. The fiberscope of claim 14 wherein said first light source is a broadband near infrared light source, said second light source is a laser, and said third light source is a broadband visible light source.

16. The fiberscope of claim 1 wherein the optical device is an optical spectrometer adapted to be used with one or more of a Raman spectra, VIS/NIR spectra or Fluorescence Spectra.

17. The fiberscope of claim 1 wherein said optical device is a chemical imaging spectrometer and detector configured to perform chemical imaging for Raman, VIS/NIR and fluorescence.

18. The fiberscope of claim 1 wherein the light received by said at least one collection fiber is scattered from said illuminated sample.

19. The fiberscope of claim 1 wherein the light received by said at least one collection fiber is Raman scattered from said illuminated sample.

20. The fiberscope of claim 1 wherein the light received by said at least one collection fiber is reflected from said illuminated sample.

21. The fiberscope of claim 1 wherein the light received by said at least one collection fiber is fluoresced from said illuminated sample.

22. The fiberscope of claim 1 wherein the light received by said at least one collection fiber has a wavelength in a range of wavelengths shifted from the illuminating wavelength by −4000 to +4000 wavenumbers (cm$^{-1}$).

23. The fiberscope of claim 1 further comprising a spatial filter disposed between said sample and said at least one collection fiber for controlling the angular field of view of said at least one collection fiber.

24. The fiberscope of claim 1 wherein the optical properties of said dichroic mirror are insensitive to temperature changes.

25. The fiberscope of claim 1 wherein the optical properties of said dichroic mirror are insensitive to humidity changes.

26. The fiberscope of claim 1 further comprising a lens disposed between said sample and said at least one collection fiber.

27. The fiberscope of claim 1 further comprising a housing for enclosing said fiberscope.

28. The fiberscope of claim 27 including a window at said distal end of said fiberscope.

29. The fiberscope of claim 28 wherein said window is substantially composed of a material selected from the group consisting of quartz, diamond, sapphire, plastic, glass, and semiconductor.

30. The fiberscope of claim 28 wherein said window includes a first portion which is spatially patterned for filtering the light from said first light source and a second portion which is transparent for the light from said illuminated sample.

31. The fiberscope of claim 1 including a switch for alternately connecting either said first or said second light source to said at least one illumination fiber,
wherein said switch connects said first light source to said illumination fiber for guiding said fiberscope to said sample and wherein said switch connects said second light source to said illumination fiber for illuminating said sample.

32. A system for imaging and collecting spectra from a sample comprising:
a near infrared ("NIR") light source;
a laser light source;
a fiberscope including:
at least one illumination fiber;
a dichroic mirror; and
at least one collection fiber; and
an optical device,
wherein said at least one illumination fiber is operatively connected at a proximate end to said NIR light source and said laser light source so as to transmit light from said light sources to said dichroic mirror disposed in proximity to a distal end of said illumination fiber, and
wherein said dichroic mirror allows light from said NIR light source to pass substantially straight through said mirror and substantially reflects light from said laser light source toward said sample to thereby illuminate said sample, and
wherein said at least one collection fiber receives light from said illuminated sample and transmits the received light to said optical device for imaging and collecting the spectra of said sample.

33. The system of claim 32 further comprising a spectral filter disposed between said sample and said collection fiber for rejecting light having a wavelength substantially the same as the wavelength of light emitted by said laser light source.

34. The system of claim 33 further comprising a spatial filter disposed between said sample and said collection fiber for controlling the angular field of view of said collection fiber.

35. The system of claim 34 further comprising a lens disposed between said sample and said collection fiber.

36. The system of claim 35 further comprising a housing for enclosing said fiberscope.

37. The system of claim 36 including a window at said distal end of said fiberscope.

38. The system of claim 37 wherein said window is substantially composed of a material selected from the group consisting of quartz, diamond, sapphire, plastic, glass, and semiconductor.

39. The system of claim 37 wherein said window includes a first portion which is spatially patterned for filtering the light from said NIR light source and a second portion which is transparent for the light from said illuminated sample.

40. The system of claim 37 including a switch for alternately connecting either said NIR light source or said laser light source to said illumination fiber,
wherein said switch connects said NIR light source to said illumination fiber for guiding said fiberscope to said sample and wherein said switch connects said laser light source to said illumination fiber for illuminating said sample.

41. The system of claim 32 wherein the optical device is an optical spectrometer adapted to be used with one or more of a Raman spectra, VIS/NIR spectra or Fluorescence Spectra.

42. The system of claim 32 wherein said optical device is a chemical imaging spectrometer and detector configured to perform chemical imaging for Raman, VIS/NIR and fluorescence.

43. The system of claim 32 wherein the light received by said collection fiber is scattered from said illuminated sample.

44. The system of claim 32 wherein the light received by said collection fiber is Raman scattered from said illuminated sample.

45. The system of claim 32 wherein the light received by said collection fiber is reflected from said illuminated sample.

46. The system of claim 32 wherein the light received by said collection fiber is fluoresced from said illuminated sample.

47. The system of claim 32 wherein the light received by said at least one collection fiber has a wavelength in a range of wavelengths shifted from the illuminating wavelength by −4000 to +4000 wavenumbers (cm$^{-1}$).

48. A method of imaging and collecting spectra from a sample, the method comprising the steps of:
providing a fiberscope including:
at least one illumination fiber operatively connected at a proximate end to a first light source and a second light source so as to transmit light from said first and second light sources to a dichroic mirror disposed in proximity to a distal end of the fiberscope;
at least one collection fiber for receiving light from said illuminated sample and transmitting the received light to an optical device; and
a dichroic mirror disposed at the distal end of the fiberscope which allows light from the first light source to pass substantially straight through the mirror and substantially reflects light from the second light source toward the sample to thereby illuminate said sample;

guiding the fiberscope using light from the first light source; and imaging and collecting spectra from the sample using light from the second source.

49. The method of claim 48, wherein the spectra is VIS/NIR.

50. The method of claim 48, wherein the spectra is fluorescence.

51. The method of claim 48, wherein the spectra is Raman.

* * * * *